United States Patent [19]
Holt et al.

[11] Patent Number: 5,778,565
[45] Date of Patent: Jul. 14, 1998

[54] VERSATILE ORTHOPAEDIC OR POST-OPERATIVE FOOTGEAR HAVING REMOVABLE TOE PIECE

[75] Inventors: Mark D. Holt, Moorepark, Calif.; Tracy E. Grim, Broken Arrow, Okla.; Stacy L. Wyatt, Camarillo, Calif.

[73] Assignee: Royce Medical Company, Camarillo, Calif.

[21] Appl. No.: 563,370

[22] Filed: Nov. 28, 1995

[51] Int. Cl.$^6$ .......................... A43B 23/26; A43B 23/00
[52] U.S. Cl. ........................ 36/110; 36/54; 36/77 R; 36/101
[58] Field of Search ...................... 36/110, 54, 77 R, 36/100, 101, 138, 105

[56] References Cited

U.S. PATENT DOCUMENTS

| | | |
|---|---|---|
| 1,012,017 | 9/1911 | Salt ............................................. 36/142 |
| 2,236,367 | 3/1941 | Gruber . |
| 2,292,297 | 8/1942 | Sherlock ..................... 36/77 R X |
| 2,444,640 | 7/1948 | Epstein . |
| 3,270,358 | 9/1966 | Milner ................................ 36/77 R |
| 3,681,860 | 8/1972 | Bidegain ............................ 36/138 |
| 3,735,758 | 5/1973 | Novotney . |
| 3,834,377 | 9/1974 | Lebold .......................... 36/110 X |
| 4,177,583 | 12/1979 | Chapman ..................... 36/110 X |
| 4,267,649 | 5/1981 | Smith . |
| 4,300,294 | 11/1981 | Riecken . |
| 4,333,248 | 6/1982 | Samuels . |
| 4,370,818 | 2/1983 | Simoglou . |
| 4,599,811 | 7/1986 | Rousseau ............................ 36/105 |
| 4,677,767 | 7/1987 | Darby ............................. 36/110 X |
| 4,773,170 | 9/1988 | Moore et al. ..................... 36/110 |
| 4,805,321 | 2/1989 | Tonkel . |
| 5,065,531 | 11/1991 | Prestridge . |
| 5,176,624 | 1/1993 | Kuehnreich . |
| 5,329,705 | 7/1994 | Grim et al. . |
| 5,483,757 | 1/1996 | Frykberg ........................ 36/54 X |

FOREIGN PATENT DOCUMENTS 2178940   2/1987   United Kingdom ................... 36/101

*Primary Examiner*—Ted Kavanaugh
*Attorney, Agent, or Firm*—Oppenheimer Wolff & Donnelly LLP

[57] ABSTRACT

Orthopaedic or post-operative footgear is provided with a removable toe piece. The toe piece is secured to the sole of the footgear to protect the toes of a user against cold, dampness, dirt and possible impact, and it is removed from the sole to allow for visual inspection of the user's toes. The toe piece can include an arcuate upper section and a substantially planar lower section, which can be secured to the sole by hook and loop material. The upper of one embodiment of the footgear is open at the toe and has overlapping flaps extending from opposite sides of the sole.

6 Claims, 4 Drawing Sheets

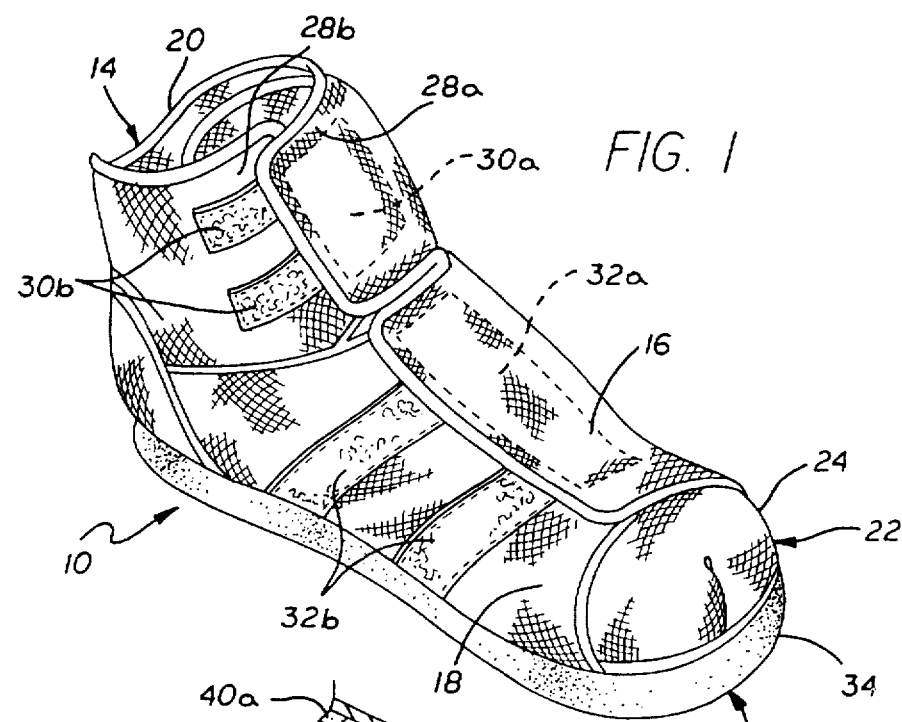
FIG. 1
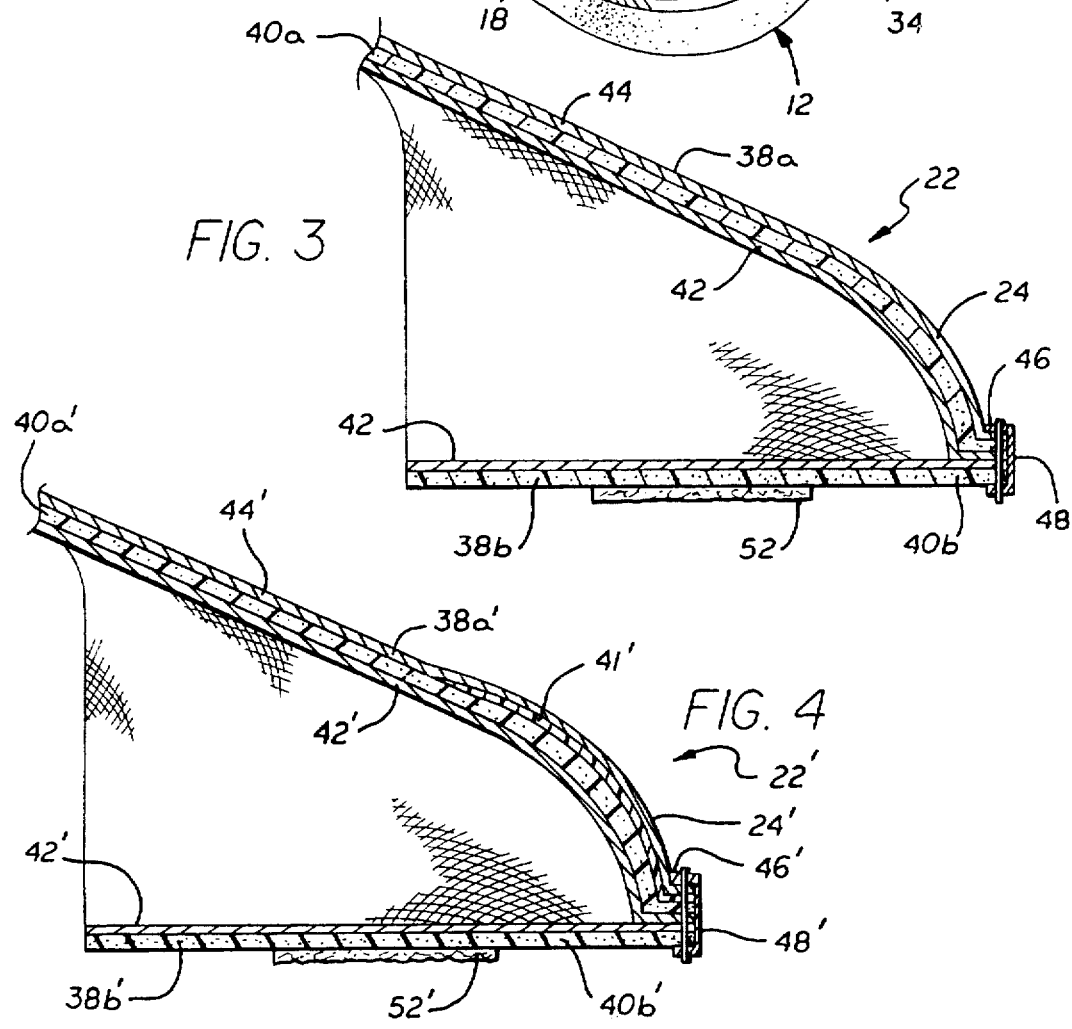
FIG. 3
FIG. 4

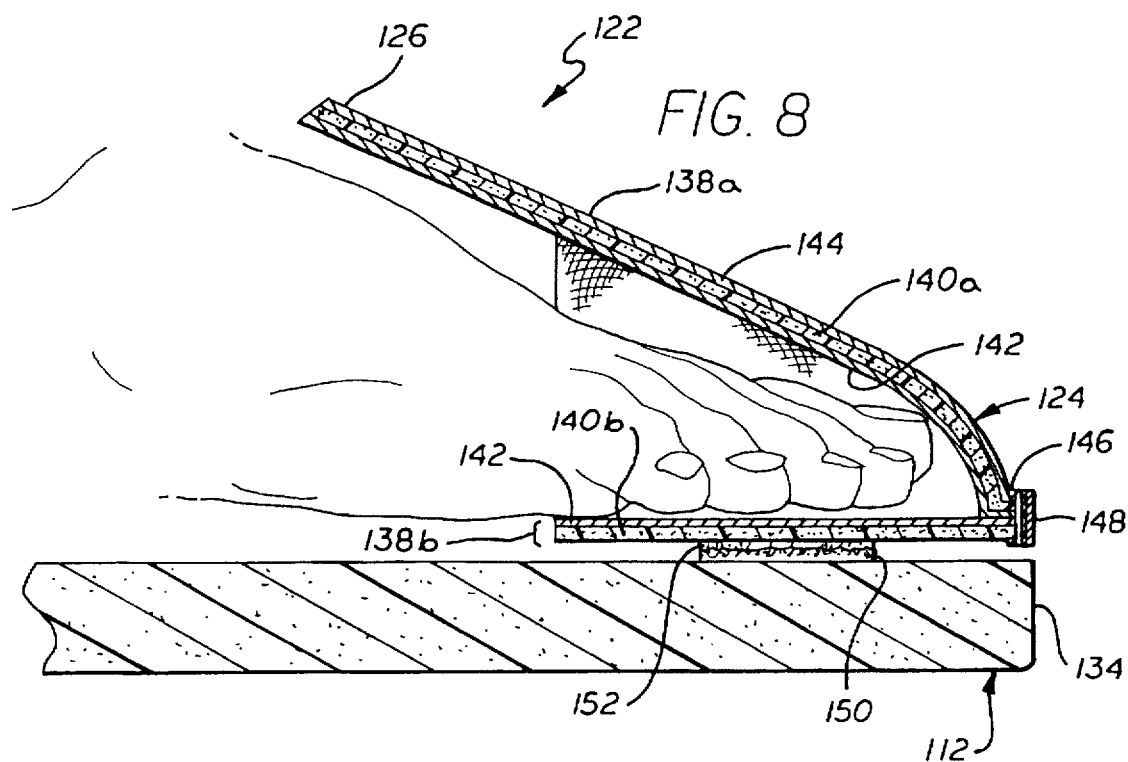
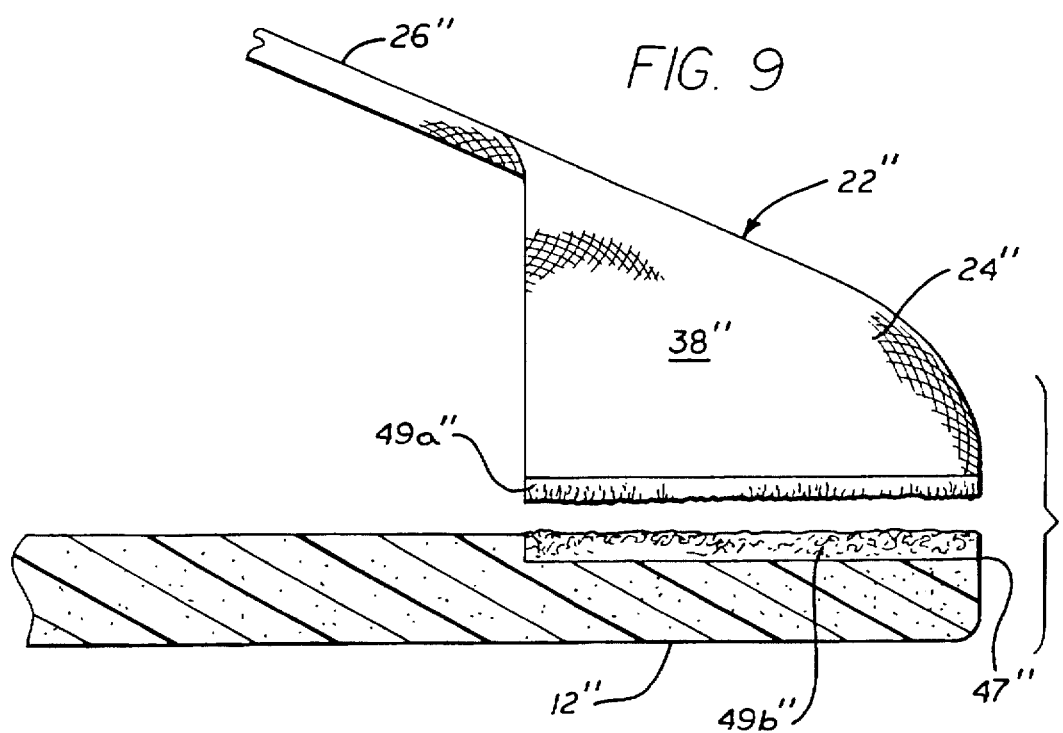

VERSATILE ORTHOPAEDIC OR POST-OPERATIVE FOOTGEAR HAVING REMOVABLE TOE PIECE

FIELD OF THE INVENTION

The present invention relates in general to footgear and in particular to an orthopaedic or post-operative shoe.

BACKGROUND OF THE INVENTION

Foot problems resulting from poor circulation, open sores, and ulcers are commonplace, particularly among geriatric patients and patients suffering from diabetes. These problems make it painful to walk and, therefore, often require surgery.

Following surgery, the foot is typically swollen and extremely tender. It may also have pins and sutures protruding from it. Protection against the environment, for example, against cold, moisture or impacts to the toe, is imperative.

In this regard, it may be desirable to have general protection for the foot, but with the toes exposed to confirm good circulation in the foot by the appearance of the toes. However, when the patient ventures into an uncontrolled environment, subject to cold, dampness or possible impact to his toes, it would be desirable to have the toes fully protected.

Riecken U.S. Pat. No. 4,300,294 discloses a sandal that can be used as a post-operative splint for the foot. The sandal includes a soft, removable cover that can be used to provide protection against inclement weather. However, the soft cover does not provide protection against impacts to the toes; and the sandal and cover combination does not permit intermediate protection for the main portion of the foot when the toes are exposed.

Darby U.S. Pat. No. 4,677,767 discloses a post-operative surgical shoe having an upper assembly that is open at the toe. Because the shoe is open at the toe, it does not protect the user's toes against cold, dampness, dirt and the like. Samuels U.S. Pat. No. 4,333,248 discloses a shoe having an impact-protective cover which overlies the toe and instep. The cover is partially removable from the shoe, but the toe portion of the shoe is not removable. Moreover, the Samuels shoe cannot be used as a post-operative shoe.

It is an object of the present invention to provide a post-operative or orthopaedic shoe which is configurable to protect a user's toes from the environment and allow for visual inspection of the toes; and which may also provide protection against impacts to the user's toes.

SUMMARY OF THE INVENTION

In accordance with a broad aspect of the invention, protective footgear includes an upper, a sole attached to the upper, and a toe piece that is removably securable to the sole at the toe. When the toe piece is secured to the sole, the footgear protects the user's toes from the environment. When the toe piece is removed from the sole, the footgear allows for visual inspection of the user's toes.

The toe piece can be flexible in construction, or it can be rigid in construction. The flexible construction provides protection against cold, dampness and dirt. The rigid construction provides additional protection against possible impacts to the user's toes.

The toe piece can include an arcuate upper section and a substantially planar lower section that is secured to the sole by hook and loop material (e.g., "VELCRO"). If the footgear is provided with an inner sole and an outer sole, the lower section of the toe piece can also be slipped between the inner and outer soles. In the alternative, the toe piece can include only an arcuate upper section that is secured to the sole by hook and loop material.

The upper of the footgear can have an open toe and overlapping flaps extending from opposing sides of the sole. In one embodiment of the footgear, the upper can also be provided with a rear portion having forwardly extending flaps for providing support for the user's ankle. In another embodiment, the overlapping flaps extend to the back of the sole and are joined thereat. In both embodiments, the flaps can fasten together by pads and/or strips of hook and loop material.

In yet another embodiment of the footgear, the upper can be of boot-like construction divided into front and rear sections, with the rear section being hinged to the rear of the sole and the front section being hinged to the front of the sole. The front section of the boot can be reinforced at the toe to protect the user's toes against possible impact. The front portion can be opened to allow for visual inspection of the user's toes.

BRIEF DESCRIPTION OF THE DRAWINGS

FIG. 1 is a perspective view of a first embodiment of a shoe according to the present invention;

FIG. 3 is a partial cross-sectional view of the toe assembly for the shoe shown in FIGS. 1 and 2, the section being taken across lines 3—3 in FIG. 2.

FIG. 4 is a partial cross-sectional view of another embodiment of the toe assembly for the shoe shown in FIGS. 1 and 2;

FIG. 8 is a schematic cross-sectional view of the shoe shown in FIGS. 5 and 6; and FIG. 9 is a schematic partial cross-sectional view of yet another embodiment of the toe assembly.

DETAILED DESCRIPTION OF THE PREFERRED EMBODIMENTS

Figure 2:
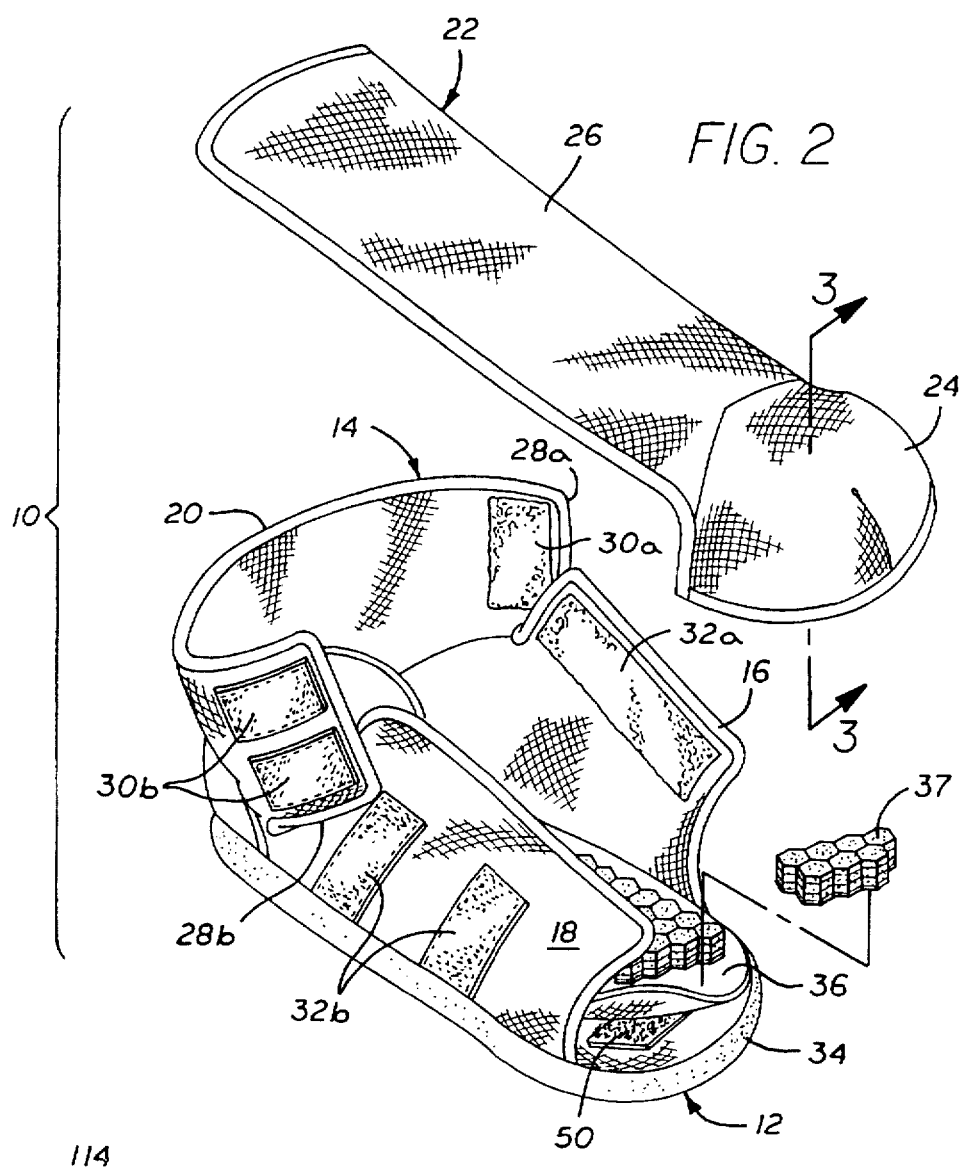
FIG. 2 is another perspective view of the shoe shown in FIG. 1, with the toe assembly being removed from the shoe.

FIGS. 1–3 show a shoe 10 including a sole 12 and an upper 14 for securing the sole 12 to the foot of a user. The upper 14 is open at the toe and includes first and second overlapping flaps 16 and 18 upwardly extending from opposite sides of the sole 12. The upper 14 also includes a rear portion 20 extending from the back of the sole 12, with overlapping forwardly extending flaps 28a and 28b.

The shoe 10 also includes a removable toe assembly 22 for protecting the user's toes against cold, dampness, dirt, possible impact and the like. The toe assembly 22 includes a toe piece 24 and a tongue 26. The toe piece 24 of the toe assembly 22 is securable to, and removable from, the front of the sole 12.

The first and second flaps 16 and 18 and the forwardly extending flaps 28a and 28b can be closed around the user's foot, even if the foot is swollen, bandaged, pinned or otherwise too large to be inserted into a closed shoe. The first and second flaps 16 and 18 are sized to overlap one another when closed over the user's instep. They may be of equal shape and dimension. The rear portion 20 is designed to provide support for the user's ankle. The forwardly extending flaps 28a, 28b of the rear portion 20 are sized to overlap one another when wrapped around the user's ankle.

The first and second flaps 16 and 18 and rear portion 20 of the upper 14 can be made of canvas, cloth, nylon, leather, rubber, or any other material used for the uppers of sneakers, shoes or boots. However, flexible material is preferable as it would allow the first and second flaps 16 and 18 and rear portion 20 to conform to the contour of the user's foot. The upper 14 could also include an inner liner (not shown) for added comfort to the user's foot. An exemplary construction for the overlapping flaps 16 and 18 and the rear portion 20 could include inner and outer walls made of a nylon mesh and an inner liner of plastic foam laminated between the two walls of nylon. The first and second flaps 16 and 18 could be stitched to, adhered to, formed integrally with, or attached to the sole 12 by any other conventional techniques.

The forwardly extending flaps 28a and 28b of the rear portion 20 are fastened together by a first pair of fasteners 30a, 30b, and the first and second flaps 16 and 18 are fastened together by a second pair of fasteners 32a, 32b. The first and second pairs of fasteners 30a, 30b, 32a and 32b could include pads and strips of hook and loop type material, such as the material sold under the trademark "VELCRO". For example, strips 32b of hook material could be secured to the outer surface of the second flap 18, and an elongated pad 32a of loop material could be secured to an inner surface of the first flap 16. Of course, the location of the mating pads could be interchanged with strips 32b being of loop type material, and pads 32a being of hook type configuration. Similarly, pads 30a, 30b of hook and loop material could be secured to the forwardly extending flaps 28a, 28b of the rear portion 20 of the upper 14. Although "VELCRO" fasteners are preferred, any other suitable fasteners, such as shoelaces and eyelets, or D-loops or buckles and straps, may be used.

The sole 12 may include an outer sole 34 that is of sufficient stiffness to provide firm support for the user's foot. For traction, an outer tread portion or crepe pattern (not shown) may be provided in the outer sole 34. For providing better balance, a heel (not shown) could be provided as part of the outer sole 34. The sole 12 could also include an inner sole 36 for providing orthopaedic support and comfort to the user's foot. The inner sole 36 could include a foam pad, an air cushion, or an air bladder covered by an upper layer of resilient material such as a poron pad. FIG. 2 shows the inner sole 36 as being a poron pad having a plurality of hexagonal elements 37. The hexagonal elements 37 can be removed to provide specific zones of pressure relief to the user's foot. This is especially comforting to diabetic patients having ulcerated appendages. The outer sole 34 could be provided with a recess for receiving the inner sole 36, making the inner sole 36 removable from the shoe 10. In the alternative, the inner sole 36 could be secured to the outer sole 34 by means such as a pressure-sensitive adhesive, provided that the toe area of the inner sole 36 can be folded back. The reasons for folding back the toe area of the inner sole 36 will soon become apparent. The construction of the insole 36 is described in greater detail in Grim et al. U.S. Pat. No. 5,329,705, issued on Jul. 19, 1994 to the assignee of the present invention. U.S. Pat. No. 5,329,705 is incorporated herein by reference.

Referring specifically to FIG. 3, the toe piece 24 of the toe assembly 22 is shown in greater detail. The toe piece 24 is essentially a hollow cup that is sized to cover the user's toes and may be about 1 or 2 inches from front to back. The toe piece 24 includes an arcuate-shaped upper section 38a and a substantially planar lower section 38b. The upper section 38a includes a first layer 40a made of a material and thickness required to protect the toes from the environment. For example, the first layer 40a of the upper section 38a can be made of a rigid material such as an impact-resistant plastic for protecting the toes against impacts. Alternatively, the first layer 40a can be a flexible material that does not provide protection against impacts to the user's toes, but does offer protection against cold, dampness and dirt. A flexible material such as cloth may be provided to hold down the user's toes and provide greater comfort to the user. The lower section 38b also includes a first layer 40b made of the same material as the first layer 40a of the upper section 38a. It must be noted that the thickness of the first layers 40a and 40b are depicted schematically in FIG. 3, and that the thickness of the first layer 40a of the upper section 38a is much thicker than the first layer 40b of the lower section 38b. The first layer 40b of the lower section is made very thin and flat so as to fit under the user's toes without causing discomfort.

The toe piece 24 can also include an inner liner 42. Different types of inner liners 42 could be utilized, depending on the desired function. A liner 42 made of sheepskin, for example, would provide maximum comfort, while a liner 42 made of nylon would provide insulation against the cold and dampness. Although the inner liner 42 is shown as covering the entire inner surface of the toe piece 24, it may cover only a portion thereof. For example, the inner liner 42 may cover only the inner surface of the upper section 38a and not the lower section 38b. The inner liner 42 could be attached to the first layer 40a and 40b by means such as a pressure sensitive adhesive or it could be stitched to the first layer 40a and 40b. The inner liner 42 is also depicted schematically in FIG. 3. If the inner liner 42 covers the inner section of the lower section 38b, the inner liner 42 must be made very thin and flat so as not to cause discomfort to the user's toes.

The outer surface of the first layer 40a of the upper section 38a could be covered by a decorative layer 44, such as a decorative fabric.

The upper section 38a terminates in a flange 46 that is secured to the lower section 38b at a binding 48. Alternatively, the upper and lower sections 38a and 38b could be integrally formed, or they could be fastened together with an adhesive.

The tongue 26 can be attached to the first layer 40a of the upper section 38a or it can be formed as an extension of the first layer 40a. The tongue 26 is preferably made of the same material as the first and second flaps 16 and 18 (that is, woven material, nylon, canvas, leather, or similar materials).

The toe piece 24 may be secured to the sole 12 by folding back the toe area of the inner sole 36 and slipping the lower section 38b between the inner and outer soles 34 and 36. The toe piece 24 may be further secured to the inner sole 36 by, for example, a pad 50 of hook or loop material attached to the outer sole 34 (see FIG. 2) and a mating pad 52 of hook or loop material on the lower section 38b.

The shoe 10 can be worn with or without the toe assembly 22. To wear the shoe 10 with the toe assembly 22, the toe piece 24 is secured to the sole 12 before the upper 14 is closed around the user's foot and ankle. After the toe assembly 22 is secured to the sole 12, the upper 14 is opened by pulling apart the first and second flaps 16 and 18 and the rear portion 20. The tongue 26 is pulled back, and the user's foot is placed on the insole 36, with the toes inside the toe piece 24. Then, the tongue 26 is extended over the user's instep and the upper 14 is closed around the user's foot by wrapping forwardly extending flaps 28a, 28b of the rear portion 20 around the user's ankle and fastening them together with the first pair of fasteners 30a, 30b, closing the second flap 18 over the tongue 26, closing the first flap 16 over the second flap 18, and fastening the first and second flaps 16 and 18 together with the second pair of fasteners 32a, 32b.

Once the shoe 10 is secured to the user's foot, the user is free to walk about, even shortly after surgery. Even though the user's foot might be swollen, bandaged or tender, the toes are protected against cold, dampness and possible impact.

The toe assembly 22 offers additional advantages. The toe piece 24 makes the shoe 10 a bit more "fashionable" then a conventional protective shoe, which has an open toe portion exposing the user's toes. Additionally, the toe piece 24 protects the toes from dirty areas.

The shoe 10 is also versatile because it can be worn without the toe assembly 22. The toe assembly 22 is removed from the shoe 10 by unfastening and pulling apart the first and second flaps 16 and 18 and the rear portion 20, and pulling the toe piece 24 away from the sole 12. The flaps 16 and 18 and rear portion 20 are then closed around the user's foot and fastened together with the fasteners 30a, 30b, 32a and 32b. This configuration is best suited for a controlled environment in which the user's toes are not subject to dampness, cold, dirt or possible impact. It offers the advantage of allowing visual inspection of the user's toes, the appearance of which indicates the circulation of blood in the foot. It also offers the advantages of being more comfortable to wear and exposing the foot to fresh air.

In another embodiment of the toe assembly 22', as shown in FIG. 4, a first layer 40a' is made of a flexible material and an insert 41' made of a rigid material is disposed between an outer liner 44' and the first layer 40a'. The insert 41' could be made of a rigid plastic. It can be of any size or shape, covering the entire toe or only a portion thereof. For example, the insert 41' could be a single stay. There are numerous ways of securing the insert 41' to the first layer 40a'. For example, the insert 41' could be attached to an outer surface of the first layer 40a' or embedded within the first layer 40a', or a section of the first layer 40a' could be hardened, or a section of the first layer 40a' could be removed and replaced with the insert 41'.

FIG. 9 shows yet another embodiment of a toe assembly 22". The toe assembly includes a toe piece 24" having an arcuate shaped upper section 38" and a tongue 26" extending from the upper section 38". A substantially planar lower section for the toe piece 24" could be provided, but is not necessary. The upper section 38" is secured to a lip 47" on the sole 12" by strips 49a", 49b" of hook and loop material on the contacting areas of the toe piece 24" and the sole 12". The strip 49b" is on the outer surface of the sole 12," and the strip 49a" is on the inner surface of the upper section 38". The toe piece 24" is held in place when the flaps of the upper are closed over the tongue 26". This toe assembly 22" is of a simpler construction than the toe assemblies 22 and 22' shown in FIGS. 3 and 4 and, therefore, easier to manufacture.

Figure 5:
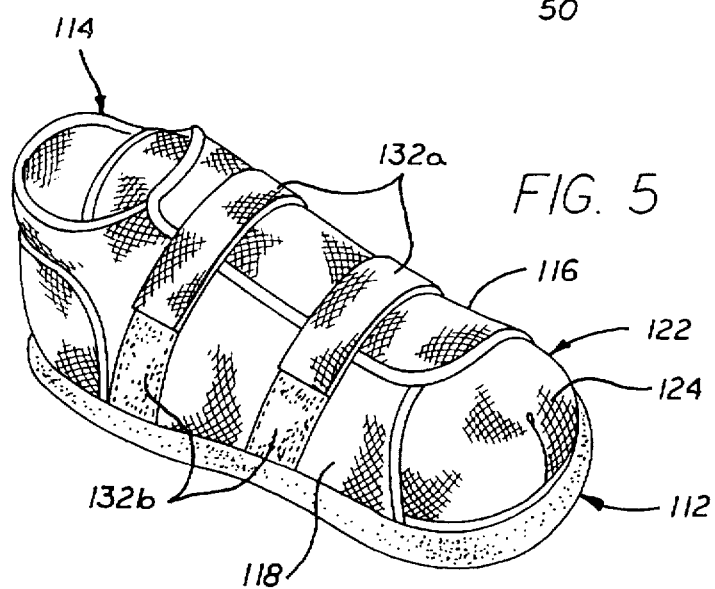
FIG. 5 is a perspective view of another embodiment of a shoe according to the present invention.
Figure 6:
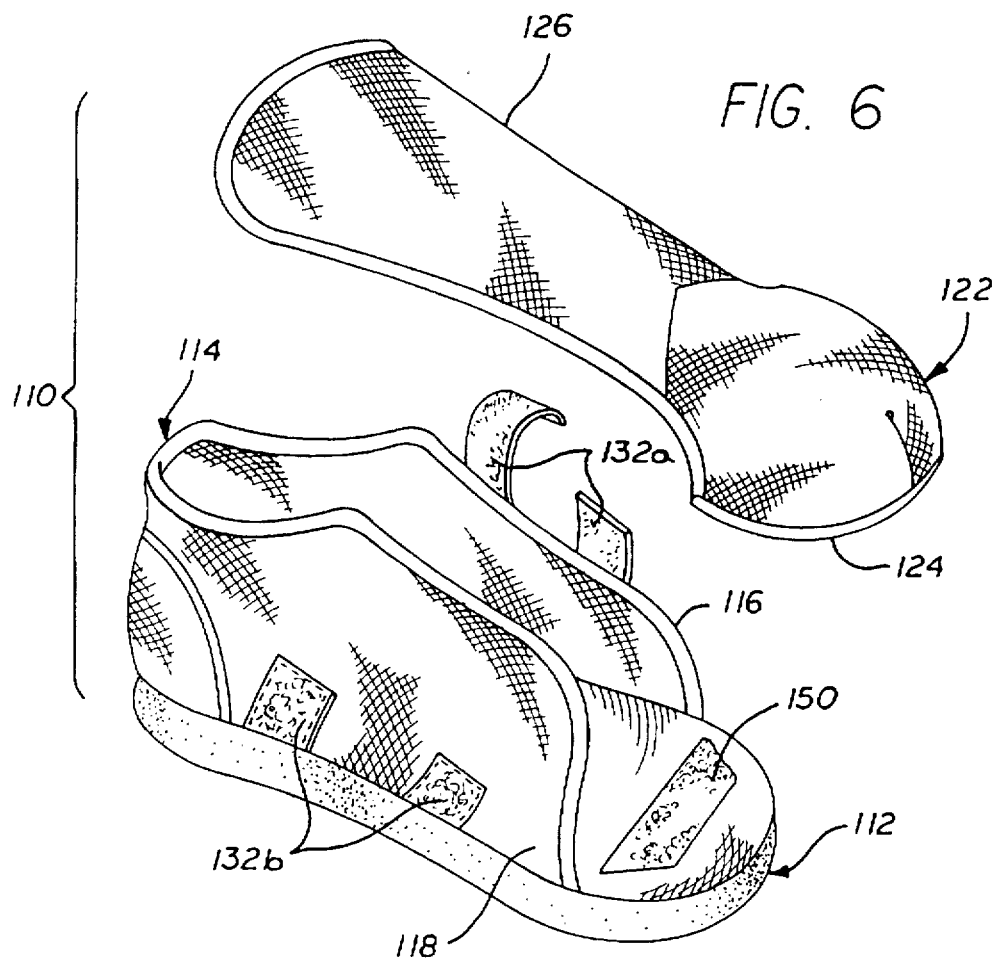
FIG. 6 is another perspective view of the shoe shown in FIG. 5, with the toe assembly being removed from the shoe.

FIGS. 5, 6 and 8 show another embodiment of a shoe 110 according to the present invention. The upper 114 of the shoe 110 is of a "low-top" construction and includes a unitary flap that extends along one side of the sole 112 to the heel (first section 116) and from the heel to the other side of the sole 112 (second section 118). The toe area is open. Moreover, the sole 112 does not include a separate removable inner sole. The toe assembly 122 is secured to the sole 112 by mating a pad 150 of hook or loop material on the sole 112 and a mating pad of hook or loop material (not shown) on the lower section of a toe piece 124. The user's foot is placed on the sole 112, with the toes inside the toe piece 124 and a tongue 126 extended over the user's instep. In FIG. 8., the thicknesses of the upper section 138a and lower section 138b of the toe piece 124 are shown schematically; the upper section 138a must be made of sufficient thickness to protect the user's toes against the environment, and the lower section 138b must be made flat and thin so as to fit under the user's toes without causing discomfort. The upper 114 is fastened to the user's foot by closing the first and second sections 116 and 118 over the user's instep and fastening the two sections 116 and 118 together with a fastener arrangement 132a, 132b. In this embodiment, the fastener arrangement includes a pair of straps 132a secured to an outer surface of, and extending from, the first section 116 and a pair of mating strips 132b secured to an outer surface of the second section 118.

It is noted in passing that the shoe 110 has a simpler design, making it easier to manufacture.

Figure 7:
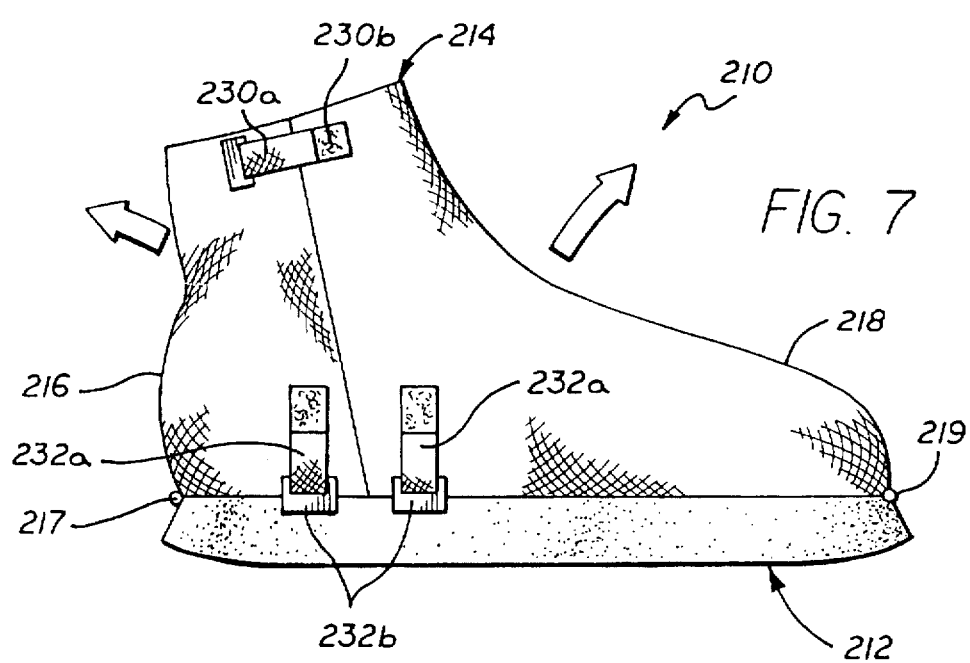
FIG. 7 is a perspective view of a yet another embodiment of a shoe according to the present invention.

FIG. 7 shows yet another embodiment of a shoe 210 according to the present invention. An upper 214 is split into a rear portion 216 that is hinged to the back of the sole 212 by a hinge 217 and a front portion 218 that is hinged to the tip of the sole 212 by another hinge 219. For convenience, the hinges 217 and 219 are shown as circles. The hinges 217 and 219 are preferably made of a flexible material attached between the upper 214 and the sole 212. However, rigid material or even mechanical hinges could be used. The rear and front portions 216 and 218 are secured together by a first fastener arrangement 230a, 230b, and they are secured to the sole 212 by a second fastener arrangement 232a, 232b. These fastener arrangements can be formed from hook and loop materials. Unlike the uppers 14 and 114 of the shoes 10 and 110 described above, the upper 214 of the shoe 210 is closed at the toe. The toe portion of the upper 214 can be reinforced with a rigid insert for protection against impacts, or it can be steel-tipped for maximum protection. Incidentally, the toe portion or toe piece may be removed from its closed configuration by pivoting the front portion 218 about the hinge point 219, where it is securable to the sole 212.

To its advantage, the shoe 210 does not require a separate toe assembly. Additionally, the boot-like construction provides a snug fit, which reduces shearing and better holds the user's foot to the sole 212.

In conclusion, a number of illustrative embodiments of the present invention have been discussed hereinabove. However, it is understood that various changes and modifications may be made without departing from the spirit and scope of the invention. For example, in the upper, the flaps extending from opposing sides of the sole can be non-overlapping instead of overlapping. The entire outer surface of the lower section of the toe piece can be covered entirely with "VELCRO" instead of a portion thereof. Also the soles of the various embodiments may be made either as a single unitary sole, or in any desired layered configuration. Use of the present invention is, of course, not restricted to orthopaedic or post-operative shoes, but can be used for other types of, such as walkers, boots or the like. Accordingly, the present invention is not limited to the precise embodiments described hereinabove.

What is claimed is:

1. A versatile orthopaedic or postoperative shoe comprising:
 a sole having a front area, a middle area and a rear area, said sole comprising an inner sole having a plurality of removable pressure-relief zone elements arranged in a grid pattern;
 an upper secured to the sole, the upper including at least two flaps;
 a fastener arrangement on at least one of the flaps, the arrangement allowing the flaps to be fastened together;
 a removable toe piece having a front portion and a rear portion, the front portion of the toe piece being securable to the sole at the front area of the sole; and
 a tongue extending from substantially the front portion of the toe piece to the rear portion thereof;
 wherein the upper is open over the toe area of the sole to expose the user's toes; and
 wherein the toe piece includes an arcuate upper section and a substantially planar lower section, the lower section being securable to the sole, whereby the user's toes are to extend between the upper and lower sections;
 whereby the toe piece may be secured to the sole at the front area to protect the toes of a user in an uncontrolled environment, and the toe piece and tongue may be removed from the sole to provide for comfort and allow for visual inspection of the user's toes.

2. A shoe as defined in claim 1, wherein said sole further comprises an outer sole and wherein at least the front area of the inner sole is separable from the outer sole, and wherein the lower section of the toe piece is placed between the inner and outer soles when the toe piece is secured to the front area of the sole.

3. A shoe as defined in claim 1, wherein said toe piece is made of a flexible material.

4. A shoe as defined in claim 1, wherein said arcutate upper section comprises rigid material.

5. A shoe as defined in claim 1, wherein said toe piece is reinforced with a rigid insert.

6. A shoe as defined in claim 1, wherein said pressure relief zone elements are hexagonal.

* * * * *